(12) United States Patent
Aydin

(10) Patent No.: US 10,408,372 B2
(45) Date of Patent: Sep. 10, 2019

(54) FLUID-CONNECTING ELEMENT

(71) Applicant: Parker Hannifin Manufacturing Germany GmbH & Co. KG, Bielefeld (DE)

(72) Inventor: Tolga Aydin, Bad Wimpfen (DE)

(73) Assignee: Parker Hannifin Manufacturing Germany GmbH & Co. KG, Bielefeld (DE)

( * ) Notice: Subject to any disclaimer, the term of this patent is extended or adjusted under 35 U.S.C. 154(b) by 2 days.

(21) Appl. No.: 15/868,477

(22) Filed: Jan. 11, 2018

(65) Prior Publication Data

US 2018/0135789 A1 May 17, 2018

Related U.S. Application Data

(63) Continuation of application No. 14/505,203, filed on Oct. 2, 2014, now Pat. No. 9,903,519, which is a
(Continued)

(30) Foreign Application Priority Data

Apr. 3, 2012 (DE) ........................ 10 2012 205 490

(51) Int. Cl.
| F16L 37/30 | (2006.01) |
| F16F 1/18 | (2006.01) |
| A61M 39/26 | (2006.01) |
| A61M 39/10 | (2006.01) |

(52) U.S. Cl.
CPC ............. *F16L 37/30* (2013.01); *A61M 39/10* (2013.01); *A61M 39/26* (2013.01); *F16F 1/18* (2013.01);
(Continued)

(58) Field of Classification Search
CPC ...... F16K 31/0693; F16K 1/482; F02B 37/16; Y02T 10/144; F16L 37/30; F16F 1/30;
(Continued)

(56) References Cited

U.S. PATENT DOCUMENTS

| 4,421,296 A | 12/1983 | Stephens |
| 4,763,683 A | 8/1988 | Carmack |

(Continued)

FOREIGN PATENT DOCUMENTS

| DE | 693 23 893 | 11/1999 |
| DE | 20 2004 014130 U1 | 2/2005 |

(Continued)

*Primary Examiner* — William M McCalister
*Assistant Examiner* — Patrick C Williams
(74) *Attorney, Agent, or Firm* — Muncy, Geissler, Olds & Lowe, P.C.

(57) ABSTRACT

A fluid-connecting element with a first receiving space with a first connecting element and a first displaceable valve element, and a second receiving space with a second connecting element and a second displaceable valve element. A fluid connection between the first receiving space and the first connecting element being interrupted by the first valve element in the first position, and a fluid connection between the first receiving space and the first connecting element being opened by the first valve element in the second position. The second valve element is displaceable between two positions, wherein a fluid connection between the second receiving space and the second connecting element is interrupted by the second valve element in the first position, and a fluid connection between the second receiving space and the second connecting element is opened by the second valve element in the second position.

11 Claims, 10 Drawing Sheets

Related U.S. Application Data continuation of application No. PCT/EP2013/056959, filed on Apr. 2, 2013.

(52) U.S. Cl.
CPC ............... *A61M 2039/1077* (2013.01); *A61M 2039/261* (2013.01); *A61M 2039/267* (2013.01); *Y10T 137/87917* (2015.04); *Y10T 137/87925* (2015.04)

(58) Field of Classification Search
CPC ...... A61M 2039/261; A61M 2039/262; A61M 2039/263; A61M 2039/267; A61M 2039/1077; A61M 39/26; A61M 39/10; Y10T 137/87917; Y10T 137/87925
See application file for complete search history.

(56) References Cited

U.S. PATENT DOCUMENTS

| | | | |
|---|---|---|---|
| 5,163,922 A | 11/1992 | McElveen, Jr. et al. | |
| 5,168,897 A | 12/1992 | Vanderjagt | |
| 5,316,041 A | 5/1994 | Ramacier, Jr. et al. | |
| 5,839,715 A * | 11/1998 | Leinsing | A61J 1/2096 251/149.1 |
| 5,890,517 A | 4/1999 | Laible | |
| 6,024,124 A | 2/2000 | Braun et al. | |
| 6,050,297 A | 4/2000 | Ostrowski et al. | |
| 6,302,147 B1 | 10/2001 | Rose et al. | |
| 6,364,869 B1 * | 4/2002 | Bonaldo | A61M 39/045 604/167.04 |
| 6,705,591 B2 | 3/2004 | deCler | |
| 7,182,313 B2 | 2/2007 | Doyle | |
| 7,815,168 B2 | 10/2010 | Vangsness et al. | |
| 7,909,056 B2 | 3/2011 | Truitt et al. | |
| 2010/0176162 A1 | 7/2010 | Hanssen | |
| 2010/0249723 A1 | 9/2010 | Fangrow, Jr. | |
| 2011/0028915 A1 | 2/2011 | Siopes et al. | |
| 2011/0276035 A1 | 11/2011 | Frangrow, Jr. et al. | |

FOREIGN PATENT DOCUMENTS

| | | |
|---|---|---|
| WO | WO 98/11931 A1 | 3/1998 |
| WO | WO 2011/100187 A1 | 8/2011 |

\* cited by examiner

FLUID-CONNECTING ELEMENT

This nonprovisional application is a continuation of U.S. application Ser. No. 14/505,203 filed on Oct. 2, 2014, which is a continuation of International Application No. PCT/EP2013/056959, which was filed on Apr. 2, 2013, and which claims priority to German Patent Application No. DE 10 2012 205 490.1, which was filed in Germany on Apr. 3, 2012, and which are both herein incorporated by reference.

BACKGROUND OF THE INVENTION

Field of the Invention

The present invention relates to a fluid-connecting element, in particular to connect vessels and to produce a fluid connection between vessels or elements that are attached to the connecting element.

Description of the Background Art

Especially in medical applications, it is known in the conventional art for liquid solutions or medicines to be taken up from a storage vessel by means of syringes and administered to patients. To this end, it is known that, using the syringe, the fluid is taken up directly through the needle of the syringe and then administered directly to the patient.

It is also known that a connecting element is placed on the storage vessel, to which connecting element the syringe can then be attached in order to draw the liquid out of the storage vessel into the syringe. When the syringe is then removed from the connector again, liquid can nevertheless leak out of the syringe, which is very disadvantageous, especially in the case of very expensive medicines. In addition, contamination is possible in this case, because escaping medicines or liquids can be lost, which is considered disadvantageous in the medical and nursing fields.

It is also known that infusion solutions, in particular, can be connected to a needle by means of tubing, wherein medicines can be added into such tubing or needles as well. This is then accomplished through a connecting element that is subject to the same disadvantages as described above.

SUMMARY OF THE INVENTION

It is therefore an object of the present invention to provide a connecting element that permits a secure connection and nonetheless allows a secure and leak-proof closure of the connected vessel when there is no connection. It is also an object of the invention to create an elastic spring element that permits secure sealing while simultaneously being simple in design.

An exemplary embodiment of the invention provides a connecting element with a housing having a first receiving space with a first connector element and a first displaceable valve element located therein, and having a second receiving space with a second connector element having a second displaceable valve element located therein, the first and second receiving spaces are fluidically connected to one another, wherein the first valve element is displaceable in opposition to the force of a first force accumulator and the second valve element is displaceable in opposition to a second force accumulator, wherein the first valve element is displaceable between two positions, wherein a fluid connection between the first receiving space and the first connector element is interrupted by the first valve element in the first position, and a fluid connection between the first receiving space and the first connector element is opened by the first valve element in the second position, and wherein the second valve element is displaceable between two positions, wherein a fluid connection between the second receiving space and the second connector element is interrupted by the second valve element in the first position, and a fluid connection between the second receiving space and the second connector element is opened by the second valve element in the second position.

This has the effect that the first receiving space can be connected to a vessel that is attachable to the first connector element, and the second receiving space can be connected to a vessel that is attachable to the second connector element, wherein, in the event no connection is made to the applicable connector element, the connector element is closed accordingly by means of the valve element located with regard thereto. The result achieved by this means is that the connecting element produces a fluid passage when there is a vessel connected to both connector elements. If only one vessel is connected, the connector element to which no vessel is attached is closed. This has the effect that the vessel in this operating state is sealed even when a connecting element is located thereon.

A "Vessel" can be, for example, a syringe, a bottle, a tube, a bag, or the like, in which a liquid can be accommodated.

An exemplary embodiment of the invention provides a connecting element with a housing having a first receiving space with a first connector element and having a second receiving space with a second connector element having a second displaceable valve element located therein, the first and second receiving spaces are fluidically connected to one another, wherein the second valve element is displaceable in opposition to a second force accumulator, wherein the second valve element is displaceable between two positions, wherein a fluid connection between the second receiving space and the second connector element is interrupted by the second valve element in the first position, and a fluid connection between the second receiving space and the second connector element is opened by the second valve element in the second position, wherein the first receiving space is fluidically connected to the first connector element.

An exemplary embodiment of the invention provides a connecting element with a housing having a first receiving space with a first connector element and a first displaceable valve element located therein, and having a second receiving space with a second connector element, the first and second receiving spaces are fluidically connected to one another, wherein the first valve element is displaceable in opposition to the force of a first force accumulator, wherein the first valve element is displaceable between two positions, wherein a fluid connection between the first receiving space and the first connector element is interrupted by the first valve element in the first position, and a fluid connection between the first receiving space and the first connector element is opened by the first valve element in the second position, wherein the second receiving space is fluidically connected to the second connector element.

In this context, it is advantageous in an exemplary embodiment for the housing to be implemented in at least two-piece form. In this design, the two parts advantageously are pressed together, interlocked, clipped together, welded, glued, or connected by other means. It is especially advantageous in this context for the two housing parts to be advantageously connected to one another, such as, in particular to be connected to one another so that they cannot be separated nondestructively.

It is also advantageous for the housing to be implemented in one piece, wherein the housing can be composed of multiple housing parts that are connected to one another, such as, in particular, to be connected to one another so that they cannot be separated nondestructively.

In the case of pressing, a connection can be achieved economically without additional elements. In this case, no foreign material interferes with the liquids that later flow through the connecting element, as well. In addition, gluing ensures a reliably leak-proof connection.

Moreover, it is useful for the first receiving space to be composed of a first housing part and a second housing part, and for the second receiving space to be composed of the second housing part. In this design, the two housing parts are connected to one another in such a way that the receiving space is produced between the two halves of the housing. This can advantageously be accomplished such that the two housing parts each have a floor with a surrounding wall, which are fitted one into the other in such a manner that the two surrounding walls contact one another and the two floors are spaced apart from one another, and thus form between them a volume to hold a liquid or to allow the liquid to pass through.

It is advantageous for the first connector element to be located or formed on the first housing part and for the second connector element to be located or formed on the second housing part. It is especially advantageous in this design for the two connector elements to be located opposite one another so that essentially linear flow results. A favorable geometry can be achieved by this means, and the pressure drop also remains low in straight-line flow, which reduces the operating forces or keeps them low, for example during filling of a syringe.

It is advantageous in accordance with the invention when the first receiving space has an approximately circular cross-section and is delimited by a surrounding wall, wherein the receiving space is delimited by two approximately flat wall regions, wherein the first connector element is located or accommodated on one of the two walls and a fluid connection to the second receiving space is provided in the other wall. The receiving space thus is advantageously approximately cylindrical with a surrounding, circumferential wall and two walls approximately opposite one another. In this design it is advantageous for the circumferential wall to be a cylindrical wall that can brace against a corresponding wall of the other housing part in order to achieve a good seal.

It is especially advantageous for the first connector element to have a hollow, cylindrical element and the first valve element to have at least one cylindrical region that is displaceably accommodated in the hollow, cylindrical element. It is advantageous in this design for the essentially cylindrical element to be made from an elastic material so that it can rest against the wall of the hollow, cylindrical element and form a seal there. When the valve element is displaced through the application of force, an edge of the cylindrical element is displaced into or past a region in which a deviation from the hollow, cylindrical contour is present or a groove is present, for example, so that a fluid connection is produced between the connector element and the receiving space.

Furthermore, it is useful for the valve element to have resilient arms projecting from the cylindrical region. In this design, the cylindrical region can have resilient arms on one side, advantageously at least three resilient arms, which project uniformly from the perpendicular, for example in the manner of the edges of a tetrahedron. It is advantageous in this design for the resilient arms to project in a uniformly distributed manner. It is also possible for more than three resilient arms, for instance four or five or more resilient arms, to project.

It is advantageous when the second receiving space has a region with a circular cross-section that is delimited by a surrounding wall, wherein the receiving space is delimited by two approximately flat wall regions, wherein the second connector element is located or accommodated on one of the two walls and a fluid connection to the first receiving space is provided in the other wall. The wall for producing a fluid connection to the first receiving space is advantageously formed by the same element that also forms the wall of the first receiving space that produces the fluid connection to the second receiving space. It is advantageous in this design if the applicable wall is located on an element, and the opposite wall to it is a plate, disk, or the like. The fluid connection is then advantageously achieved by at least one opening, advantageously a plurality of openings.

It is also advantageous for the first receiving space to have a circular cross-section with outwardly projecting pockets and to be delimited by a surrounding wall with changeable radius, wherein the receiving space is delimited by two approximately flat wall regions, wherein the first connector element is located or accommodated on one of the two walls and a fluid connection to the second receiving space is provided in the other wall. As a result of the formation of the surrounding pockets, the volume of the receiving space is reduced without impairing the function of the receiving space. This is especially advantageous in the case of costly liquids, because the liquid remaining in the receiving space is lost.

It is especially advantageous when the number of pockets corresponds to the number of resilient arms of the valve element. This is advantageous because the resilient arms can be accommodated reliably, and no additional dead volume is created.

It is especially advantageous when a resilient arm of the valve element is located in each pocket.

Furthermore, it is advantageous for a pin that engages the second connector element to project from the other wall. The pin is advantageously a flat or cylindrical bar that engages a sleeve of the second connector element. In this design, the pin advantageously has a thickened region at its end, against which the end of the sleeve is braced.

It is also advantageous when the wall with the connector element as second valve element is displaceable in opposition to the force of a force accumulator, and a fluid connection between the connector element and the pin projecting into the connector element can be opened by this means.

It is additionally advantageous when the second force accumulator is an elastic element that is located in the second receiving space.

It is useful in this design for the second force accumulator to be an elastic ring, preferably such as an elastic oval ring or O-ring.

According to an embodiment of the invention, it is advantageous when the resilient arms projecting from the cylindrical region or from the cylindrical body are implemented as straight resilient arms or as resilient arms with one or multiple bends or curves. As a result of the bending, a better contact area can be achieved and the arms better serve the function of displacing the cylindrical region or body in the vertical direction in opposition to the elastic spring force of the resilient arms.

It is especially advantageous when the resilient arms of the first valve element are arranged at an angle of 120° with respect to one another in the plane perpendicular to the longitudinal axis of the cylindrical region. To this end, it is advantageous for three resilient arms to be provided.

It is also advantageous in one exemplary embodiment when the resilient arms have a first region that is arranged at an angle of approximately 25° to 30°, preferably 27°, to the plane perpendicular to the longitudinal axis of the cylindrical region. This region advantageously is directly adjacent to the cylindrical region.

It is also advantageous for the resilient arms to have a second region that is arranged at an angle of approximately 35° to 40°, preferably 37°, to the plane perpendicular to the longitudinal axis of the cylindrical region. This region follows the first region.

It is also useful for the resilient arms to have a third region that is arranged at an angle of approximately 75° to 80°, preferably 77°, to the plane perpendicular to the longitudinal axis of the cylindrical region. This region follows the second region, and constitutes the region that stands on a wall, such as the floor, of the receiving space.

An exemplary embodiment of the invention relates to an elastic spring element with a cylindrical body and resilient arms projecting therefrom, wherein the spring element is made of an elastic material. In this design, three resilient arms, in particular, project from the cylindrical body, wherein the preferably three resilient arms are distributed at an angle of 120° in the plane perpendicular to the center axis of the cylindrical body.

It is advantageous according to the invention for the projecting resilient arms to be implemented as straight resilient arms or as resilient arms with one or multiple bends or curves. As a result of the bending or curvature, the resilient arm can be supported better while nonetheless achieving a favorable spring characteristic for the resilience of the cylindrical region.

It is especially advantageous in this design for the resilient arms of the first valve element to be arranged at an angle of 120° with respect to one another in the plane perpendicular to the longitudinal axis of the cylindrical region. In this design, it is especially advantageous for three resilient arms to be provided.

It is especially advantageous for the resilient arms to have a first region that is arranged at an angle of approximately 25° to 30°, preferably 27°, to the plane perpendicular to the longitudinal axis of the cylindrical region.

It is also advantageous for the resilient arms to have a second region that is arranged at an angle of approximately 35° to 40°, preferably 37°, to the plane perpendicular to the longitudinal axis of the cylindrical region.

It is also useful for the resilient arms to have a third region that is arranged at an angle of approximately 75° to 80°, preferably 77°, to the plane perpendicular to the longitudinal axis of the cylindrical region.

According to an embodiment of the invention, it is advantageous for the cross-section of a resilient arm to be round or oval or polygonal.

It is especially advantageous in this design for the cross-section of the resilient arm to be oval, wherein the cross-section in a plane through the midperpendicular of the spring element has a smaller diameter than the direction perpendicular thereto. In this way, a favorable bending behavior of the resilient arms can be achieved.

It is also useful for the cylindrical body to have a first circumferential sealing lip at an end region adjacent to the transition to the resilient arms.

Furthermore, it is useful for the cylindrical body to have a second circumferential sealing lip at an end region opposite the transition to the resilient arms. The sealing effect can be improved by this means.

It is also useful for the first sealing lip to be implemented as a circumferential shoulder. In this design, the shoulder transitions from a region of larger diameter to a region of smaller diameter.

It is especially advantageous for the second sealing lip to be implemented as a lip protruding from the cylindrical wall of the cylindrical body. The lip in this design projects from the cylindrical body in the radial direction.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
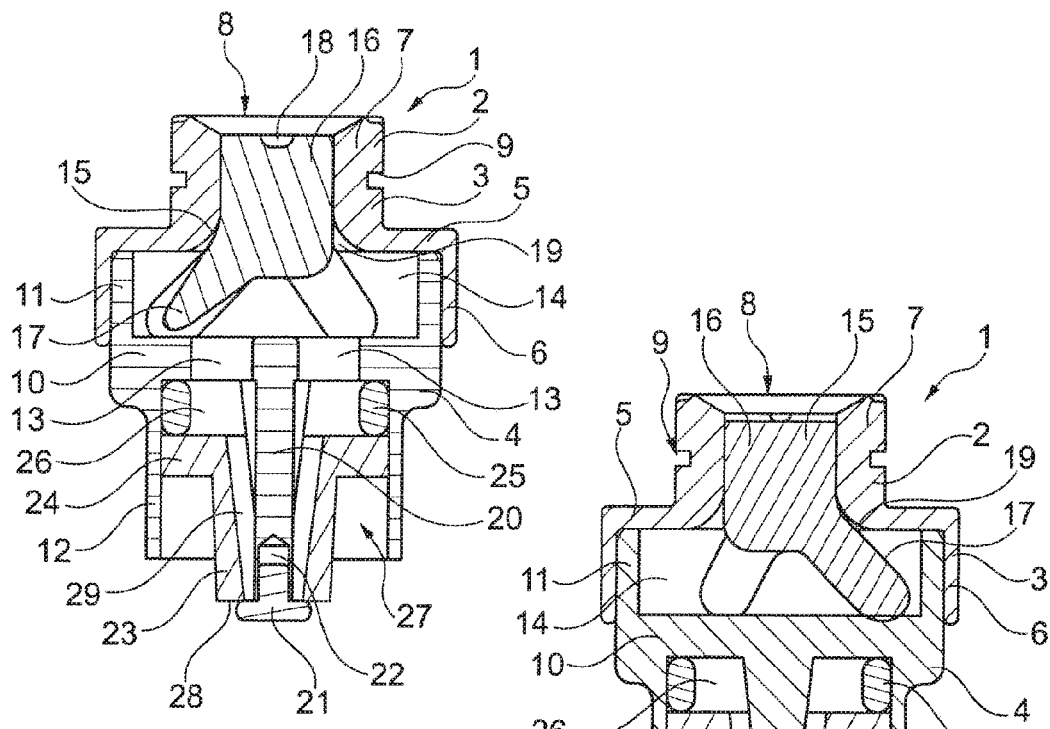
FIG. 1 is a section through a first exemplary embodiment of a connecting element according to the invention.
Figure 2:
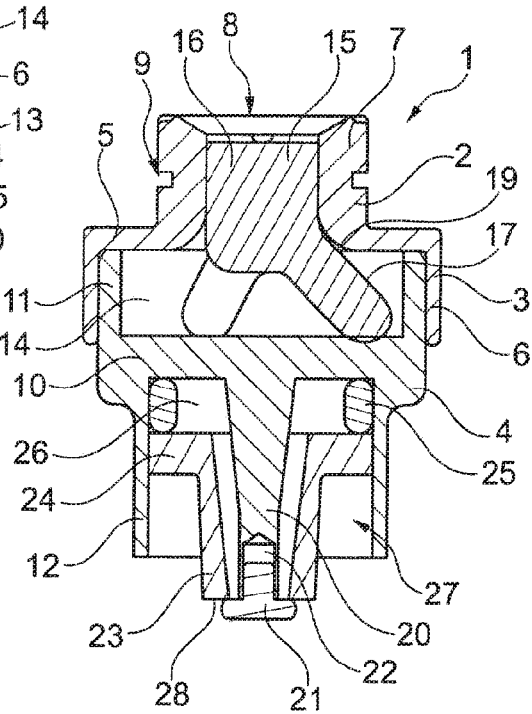
FIG. 2 is another section through the connecting element.
Figure 3:
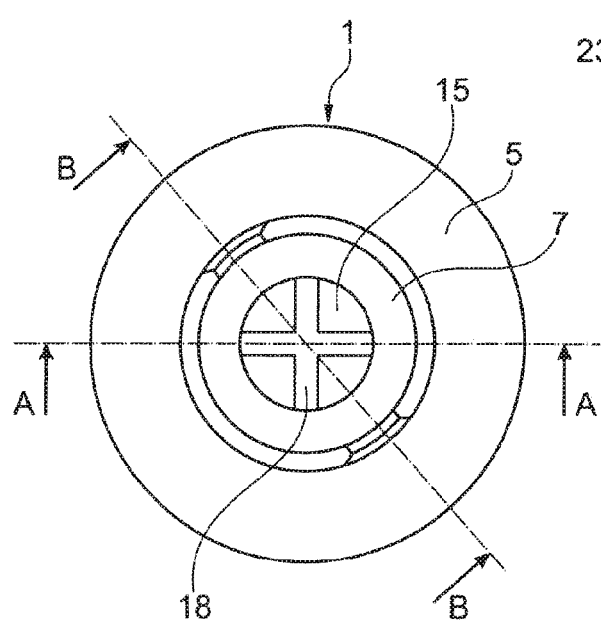
FIG. 3 is a view from above of the connecting element.

FIGS. 1 and 2 show an exemplary embodiment of a connecting element 1 according to the invention in a sectional view along lines A-A and B-B from FIG. 3. FIG. 1 shows the section along line B-B, and FIG. 2 shows the section along line A-A.

The connecting element 1 is implemented with a housing 2. The housing 2 is composed of at least two housing parts 3, 4. In the exemplary embodiment from FIG. 1, the housing 2 is composed of the two housing parts 3, 4, which are connected to one another. In other exemplary embodiments, the housing can also be implemented as a single piece or as multiple pieces with more than three housing parts.

The first housing part 3 has a floor 5 with a surrounding wall 6 projecting therefrom at an angle of 90°. The floor 5 is provided with the connector element 7. To this end, the connector element 7 is attached to the floor 5 as a connection fitting. In advantageous fashion, it is connected to the floor as a single piece. In this design, an element to be connected can be inserted into the opening 8 of the connector element 7. For the purpose of fastening, a thread 9 is provided in the wall of the fitting, radially to the outside of the connection fitting, by means of which thread the element to be connected can also be screwed to the connection fitting.

The second housing part 4 is implemented with a floor 10, from which an upwardly projecting, surrounding wall 11 extends in one direction. In the opposite direction, a surrounding wall 12 is provided that likewise projects from the floor 10. The floor 10 has openings 13 to permit fluid communication between the two sides of the floor 10. A plurality of openings are provided in the exemplary embodiment, although it is also possible to provide just one opening. Preferably, four openings 13 are provided. It is preferable for a total of four openings 13 to be provided, which are separated by a cross-shaped web.

As can be seen in FIGS. 1 and 2, the two housing parts 3, 4 are inserted one into the other in the region of the surrounding walls 6, 11, and preferably are pressed together. The walls 6, 11 are implemented such that the axial extent of the walls 6, 11 is approximately equal in length, and the inside radius of the wall 6 corresponds approximately to the outside radius of the wall 11 so that they can be inserted one into the other and pressed together.

Alternatively, the wall 6 of the first housing part 3 can also be arranged radially inside of the wall 11 of the second housing part 4.

Pressing can be advantageous for the purpose of connecting the two housing parts 3, 4 in the region of the walls 6, 11. The methods of gluing, welding, clipping, etc., may also be employed.

The housing forms a first receiving space 14 in the region of the connection of the two housing parts 3, 4, wherein the receiving space 14 is formed by a surrounding wall 11, a floor 5 of the first housing part, and a floor 10 of the second housing part.

The connector element is provided toward the top on the floor 5 of the first housing part 3, as already described above. When an element to be connected to the connector element 7, such as a syringe or the like, or a fitting affixed thereon, is inserted into the connector element 7, a fluid communication between the element to be connected and the receiving space 14 should be able to take place. If no element to be connected is inserted into the connector element, the connector element 7 should remain closed and sealed.

This is achieved with a valve element 15. The valve element 15 has a cylindrical region 16, from which resilient arms 17 project downward. In this design, the cylindrical region advantageously is implemented as a single piece with the resilient arms, and the resilient arms project radially outward at an angle of approximately 45° to the vertical and downward from the cylindrical region 16.

When three resilient arms are present, the resilient arms 17 form an arrangement like the edge arrangement of a tetrahedron. Placed at the top edge of the cylindrical region 16 is a cross-shaped groove 18, which serves to ensure a fluid connection between the connector element 7 and the receiving space 14.

In the positions of the valve element 15 shown in FIGS. 1 and 2, a fluid connection between the connector element 7 and the receiving space 14 is closed and sealed. If an element is inserted into the connector element 7 from above, then the cylindrical region 16 of the valve element 15 is compressed and pushed downward so that the resilient arms 17 bear against the corners of the receiving space 14 and are elastically deformed. This will continue to take place until a fluid connection is present between the cross-shaped channel 18 and a curvature 19 in the region of the connector element. Then a fluid connection can take place between the element to be connected and the receiving space 14. Instead of the curvature, grooves or channels can also be provided in the wall of the connector element that permit a fluid connection starting from a certain, predefinable position of the valve element.

When the element to be connected is removed from the connector element 7 again, then the elastic, deformable valve element 15 relaxes again, and the cylindrical region 16 is again pushed upward so that the connector element 7 is sealed once again.

Provided in the bottom region of the connecting element 1, radially below the cylindrical wall region 12, is a pin 20 that bears a thickened element 21 at its end, which preferably is inserted into an opening 22 of the pin 20 or preferably is made as a single piece with the pin 20. The pin 20 preferably can be formed as a single piece with a web that separates the openings 13.

A sleeve-like element 23 that transitions into a floor 24 is provided as the valve element, wherein the sleeve-like element 23 is made in the approximate shape of a hollow cylinder and its axial bottom edge region braces against a shoulder of the element 21. Located between the floor 24 and the floor 10 of the housing part is a force accumulator 25, preferably in the form of an annular, elastic element, in order to effect a loading of the sleeve-like element 23 against the element 21. As a result, a seal is achieved between the receiving space 26 and the connector element 27, which is formed by the sleeve-like element 23 with the floor 24 and the circumferential wall 12. The sleeve-like element 23 preferably is cylindrical or at least somewhat conical in design so that the top opening is larger than the bottom opening, which braces against the element 21.

When an element to be connected having a circumferential collar is inserted into the region 27 from below, the sleeve-like element 23 with the floor 24 is pushed axially upward, in opposition to the force of the force accumulator 25, and the shoulder 28 of the sleeve-like element 23 lifts away from a shoulder of the element 21 and permits a fluid connection to be made from the element to be connected, through the channel 29 in the sleeve-like element 23, to the receiving space 26. Since a fluid connection exists between the receiving space 26 and the receiving space 14 due to the openings 13, a fluid connection can be produced between two elements to be connected that are attached to the connector elements 7 and 27.

Preferably the elastic elements 15 and 25 are made of an elastomeric material, and the housing elements 3,4 as well as the sleeve-like element 23 and the element 21 are made of a non-elastomeric material that tends to be dimensionally stable, such as a thermoplastic. The element 15 and the element 25 preferably can be made of liquid silicone rubber (LSR) or high temperature vulcanized silicone rubber (HTV) or room temperature vulcanized silicone rubber (RTV), and the housing parts, sleeve, and terminating element 21 can be made of acrylonitrile butadiene styrene (ABS), polycarbonate (PC), polypropylene (PP), or polyethylene (PE), or the like.

The element 21 can be inserted into an opening in the pin 20, as shown. Alternatively, the element 21 can also be produced through hot pressing of the pin by means of a deformation of the pin in this regard. If desired, it can also be injection-molded onto the pin.

It can also be advantageous for an elastomeric material to be provided between the element 21 and the sleeve-like element 23 in the region of the shoulder of the element 21, such as a washer that can also be provided as prevulcanized material, for example, in order to achieve a better seal between the element 21 and the element 23.

Alternatively to the implementation of the force accumulator 25 as an elastomeric ring, the accumulator can be implemented as an oval ring or O-ring, for example, or else as a different form of force accumulator, such as a spring energy store, for example. In addition, the resilient arms 17 of the cylindrical element 15 can also be implemented differently as an alternative, for example by means of a central, elastic extension that extends the element 15 in the axial direction. The extension can also be provided in addition to the resilient arms.

It could also be advantageous for the element that thus far has been asymmetrical in design to be made symmetrical through the provision of two identical or essentially identical components or regions so that, for instance, the valve element 15 is arranged accordingly on both sides of the floor 10 in order to close two receiving spaces located on the two sides of the floor 10 with identical valve elements. Accordingly, two valve elements corresponding to 23, 24, which are arranged on both sides of the wall 10, could also be provided [in] the alternative arrangement. In this way, an identical valve unit located on both sides of the wall 10 could be provided that would also be easy to manufacture due to uniformity of the components.

FIG. 3 shows the connecting element 1 in a view from above, in which the floor 5 can be seen as a disk-shaped floor from which the connector element 7 projects upward in an annular shape. The valve element 15 with the cross-shaped fluid-connecting groove 18 can be seen in the central opening of the annular connector element 7.

Figure 5:
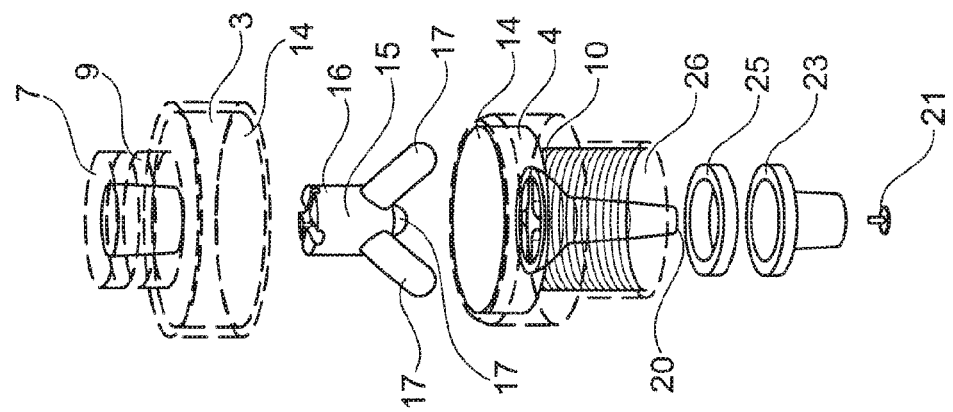
FIG. 5 is an exploded view of a connecting element.
Figure 4:
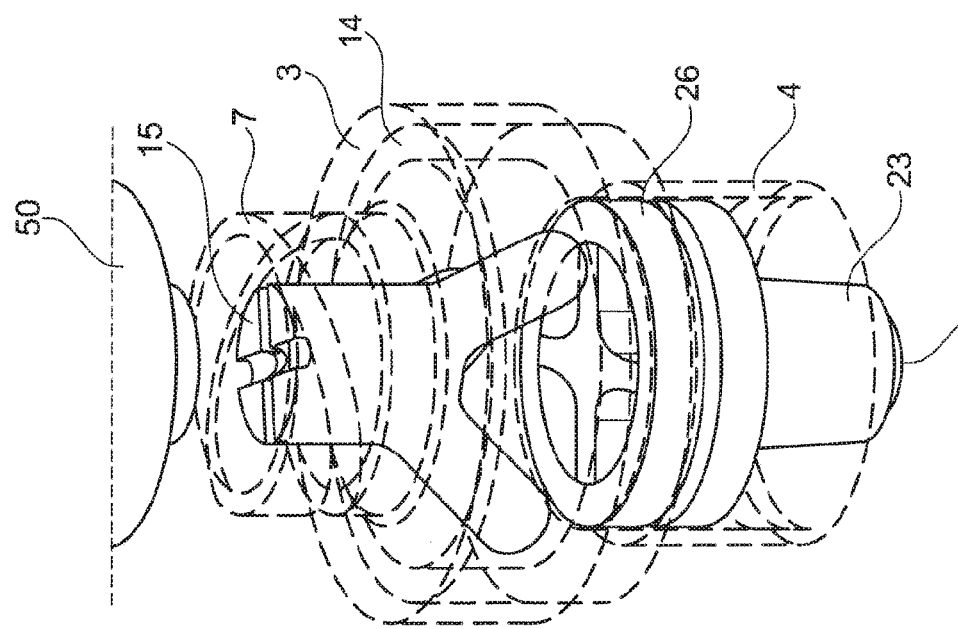
FIG. 4 is a perspective representation of the connecting element.

FIG. 4 shows the connecting element 1 according to the invention in a three-dimensional, schematic representation, and FIG. 5 shows the connecting element 1 in an exploded view.

As is evident, the housing parts 3, 4 form the housing for accommodating the valve elements 15, 23, wherein these can close the receiving spaces 14, 26.

Visible at the top of FIG. 5 is the housing part 3, which defines an essentially cylindrical spatial area 14, and at its top end has the connector element 7 as a connection fitting. A thread 9 is provided at the outer edge, or on the outer wall, of the connector element 7 for the purpose of screwing to an element to be connected. This element to be connected is shown schematically in FIG. 4 as the element 50.

The valve element 15 is designed with a cylindrical body 16 and resilient arms 17 that project at an angle to the vertical. The resilient arms 17 in the exemplary embodiment from FIG. 5 are oriented similarly to the edges of a tetrahedron. The housing 4 has a receiving space that forms the receiving space in conjunction with the receiving space 14 of the housing part 3. Below the wall 10 referred to as a floor, an additional receiving space 26 is defined, into which the elastic element 25 and the sleeve-like element 23 are placed before the thickened termination 21 of the pin 20 is inserted.

Figure 6:
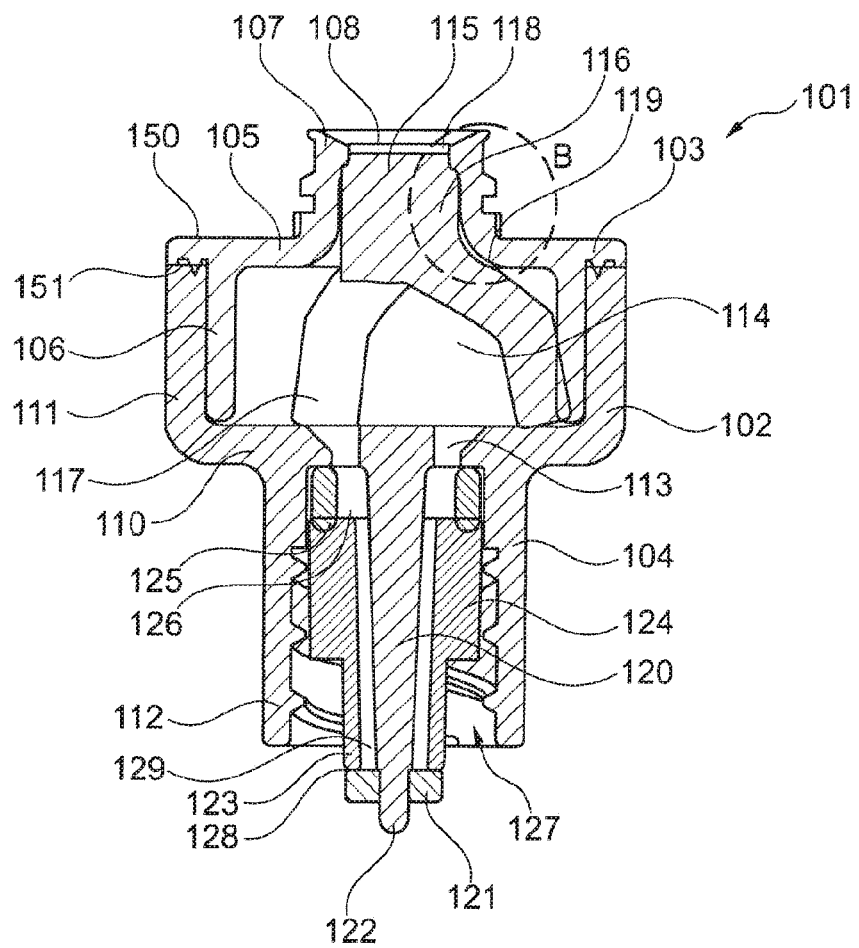
FIG. 6 is a section through another exemplary embodiment of a connecting element according to the invention.
Figures 7, 8:
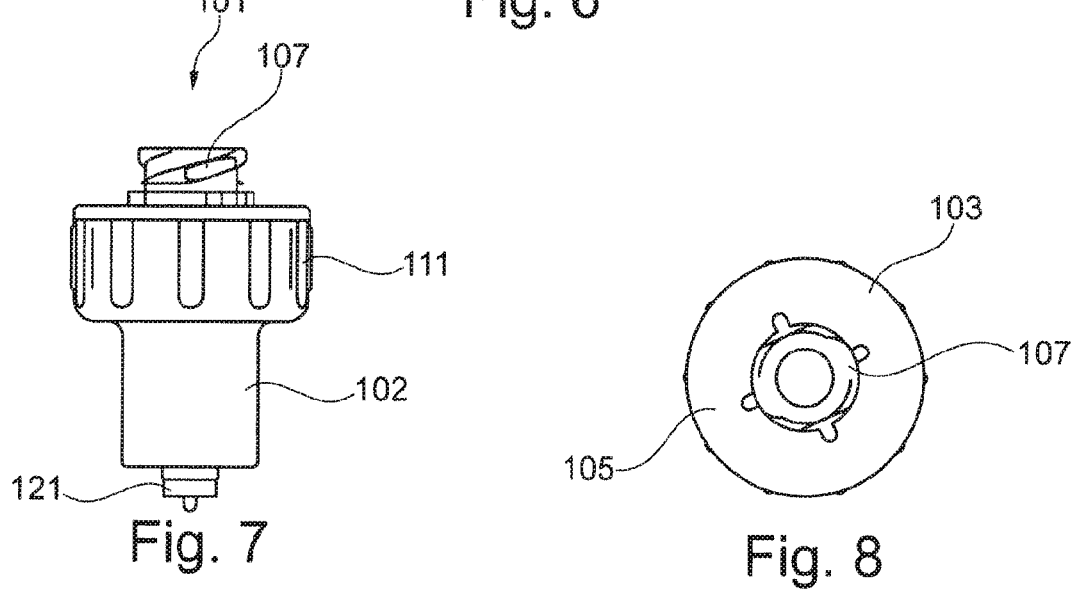
FIG. 7 is a side view of a connecting element from FIG. 6.
FIG. 8 is a view from above of the connecting element from FIG. 5 or 6.

FIGS. 6, 7, and 8 show another exemplary embodiment of a connecting element 101 according to the invention, in cross-section or in a side view or in a top view, respectively.

The connecting element 101 is implemented with a housing 102. The housing 102 consists of at least two housing parts 103, 104. In the exemplary embodiment from FIG. 6, the housing 102 is composed of the two housing parts 103, 104, which are joined to one another.

The first housing part 103 has a floor 105 with a surrounding wall 106 projecting therefrom at an angle of 90°. The floor 105 is provided with the connector element 107. To this end, the connector element 107 is attached to the floor 105 as a connection fitting. In advantageous fashion, it is connected to the floor as a single piece. In this design, an element to be connected can be inserted into the opening 108 of the connector element 107. For the purpose of fastening, a thread 109 or the like is provided in the wall of the fitting, radially to the outside of the connection fitting 107, by which means the element to be connected can also be screwed to or connected to the connection fitting 107.

The second housing part 104 is implemented with a floor 110, from which an upwardly projecting, surrounding wall 111 extends in one direction. In the opposite direction, a surrounding wall 112 is provided that likewise projects from the floor 110. The floor 110 has one or more openings 113 to permit fluid communication between the two sides of the floor 110. A plurality of openings 113 are provided in the exemplary embodiment, although it is also possible to provide just one opening. Preferably, four openings 113 are provided. It is preferable for a total of four openings 113 to be provided, which are separated by a cross-shaped web.

As can be seen in FIG. 6, the two housing parts 103, 104 are inserted one into the other in the region of the surrounding walls 106, 111, and preferably are pressed or glued together. The walls 106, 111 are implemented such that the axial extent of the walls 106, 111 is approximately equal in length, and the inside radius of the wall 111 corresponds approximately to the outside radius of the wall 106 so that they can be inserted one into the other and pressed or glued or welded together. The wall 106 is radially inside of the wall 111 in this design.

Pressing can be advantageous for the purpose of connecting the two housing parts 3, 4 in the region of the walls 6, 11. The methods of gluing, welding, clipping, etc., may also be employed. In addition, the connection can be accomplished between the flange 150 and the top 151 of the wall 111. This can also be accomplished by welding.

The housing forms a first receiving space 114 in the region of the connection of the two housing parts 103, 104, wherein the receiving space 114 is formed by a surrounding wall 106, a floor 105 of the first housing part, and a floor 110 of the second housing part.

The connector element 107 is provided toward the top on the floor 105 of the first housing part 103. When an element to be connected to the connector element 107, such as a syringe or the like, or a fitting affixed thereon, is inserted into the connector element 107, a fluid communication between the element to be connected and the receiving space 114 should be able to take place. If no element to be connected is inserted into the connector element 107, the connector element 107 should remain closed and sealed.

This is achieved with a valve element 115. The valve element 115 has a cylindrical region 116 or else a cylindrical body 116, from which resilient arms 117 project downward. In this design, the cylindrical region 116 advantageously is implemented as a single piece with the resilient arms 117, and the resilient arms 117 project radially outward at an angle to the vertical and downward from the cylindrical region 116. The elastic spring element is explained in detail in FIGS. 21 to 24. The resilient arms in the exemplary embodiment from FIGS. 6 to 8 are angled or have bends. When three resilient arms 117 are present, the resilient arms 117 form an arrangement approximating an edge arrangement of a tetrahedron.

Placed at the top edge of the cylindrical region 116 is a triangular groove 118, which serves to ensure a fluid connection between the connector element 107 and the receiving space 114 when the cylindrical element 116 is pressed downward.

In the position of the valve element 115 shown in FIG. 6, a fluid connection between the connector element 107 and the receiving space 114 is closed and sealed. If an element is inserted into the connector element 107 from above, then the cylindrical region 116 of the valve element 115 is loaded downward or compressed, and pushed downward so that the resilient arms 117 bear against the floor of the receiving space 114 and are elastically deformed. This will continue to take place until a fluid connection is present between the channel 118 and a curvature 119 in the region of the connector element. Then a fluid connection can take place between the element to be connected and the receiving space 114. Instead of the curvature, grooves or channels can also be provided in the wall of the connector element that permit a fluid connection starting from a certain, predefinable position of the valve element.

When the element to be connected is removed from the connector element 107 again, then the elastic, deformable valve element 115 relaxes again, and the cylindrical region 116 is pushed upward again so that the connector element 107 is sealed once again.

Provided in the bottom region of the connecting element 101, radially below the cylindrical wall region 112, is a pin 120 that bears a thickened element 121 at its end, into which a peg 122 of the pin 120 preferably is inserted or preferably is made as a single piece with the pin 120. The element 121 preferably is attached by means of heat staking of the peg.

The pin 120 preferably can be formed as a single piece with a web that separates the openings 113.

A sleeve-like element 123 that transitions into a floor 124 is provided as the valve element, wherein the sleeve-like element 123 is made in the approximate shape of a hollow cylinder and its axial bottom edge region braces against a shoulder of the element 121. Located between the floor 124 and the floor 110 of the housing part is a force accumulator 125, preferably in the form of an annular, elastic element such as an O-ring, in order to effect a loading of the sleeve-like element 123 against the element 121. As a result, a seal is achieved between the receiving space 126 and the connector element 127, which is formed by the sleeve-like element 123 with the floor 124 and the circumferential wall 112.

When an element to be connected having a circumferential collar is inserted into the region 127 from below, the sleeve-like element 123 with the floor 124 is pushed axially upward, in opposition to the force of the force accumulator 125, and the shoulder 128 of the sleeve-like element 123 lifts away from a shoulder of the element 121 and permits a fluid connection to be made from the element to be connected, through the channel 129 in the sleeve-like element 123, to the receiving space 126. Since a fluid connection exists between the receiving space 126 and the receiving space 114 due to the openings 113, a fluid connection can be produced between two elements to be connected that are attached to the connector elements 107 and 127.

Preferably the elastic elements 115 and 125 are made of an elastomeric material, and the housing elements 103, 104 as well as the sleeve-like element 123 and the element 121 are made of a non-elastomeric material that tends to be dimensionally stable, such as a thermoplastic. The element 115 and the element 125 preferably can be made of liquid silicone rubber (LSR) or high temperature vulcanized silicone rubber (HTV) or room temperature vulcanized silicone rubber (RTV), and the housing parts, sleeve, and terminating element 121 can be made of acrylonitrile butadiene styrene (ABS), polycarbonate (PC), polypropylene (PP), or polyethylene (PE), or the like.

FIG. 7 shows a view of the connecting element 101, while FIG. 8 shows that the receiving space 114 with the cover 105 is round in cross-section.

FIGS. 9, 10, 11, and 12 show another exemplary embodiment of a connecting element 201 according to the invention, in cross-section or in a side view or in a top view, respectively.

The connecting element 201 is implemented with a housing 202. The housing 202 consists of at least two housing parts 203, 204. In the exemplary embodiment from FIG. 9, the housing 202 is composed of the two housing parts 203, 204, which are joined to one another.

The first housing part 203 has a floor 205 with a bar 206 projecting therefrom. The floor 205 is provided with the connector element 207. To this end, the connector element 207 is attached to the floor 205 as a connection fitting. In advantageous fashion, it is connected to the floor as a single piece. In this design, an element to be connected can be inserted into the opening 208 of the connector element 207. For the purpose of fastening, a thread 209 or the like is provided in the wall of the fitting radially to the outside of the connection fitting 207, by which means the element to be connected can also be screwed to or connected to, such as plugged onto, the connection fitting 207.

The second housing part 204 is implemented with a floor 210, from which an upwardly projecting, surrounding wall 211 extends in one direction. In the opposite direction, a surrounding wall 212 is provided that likewise projects from the floor 210.

The floor 210 has at least one opening or multiple openings 213 to permit fluid communication between the two sides of the floor 210. A plurality of openings 213 are provided in the exemplary embodiment, although it is also possible to provide just one opening. Preferably, four openings 213 are provided. It is preferable for a total of four openings 213 to be provided, which are separated by a cross-shaped web.

Figure 9:
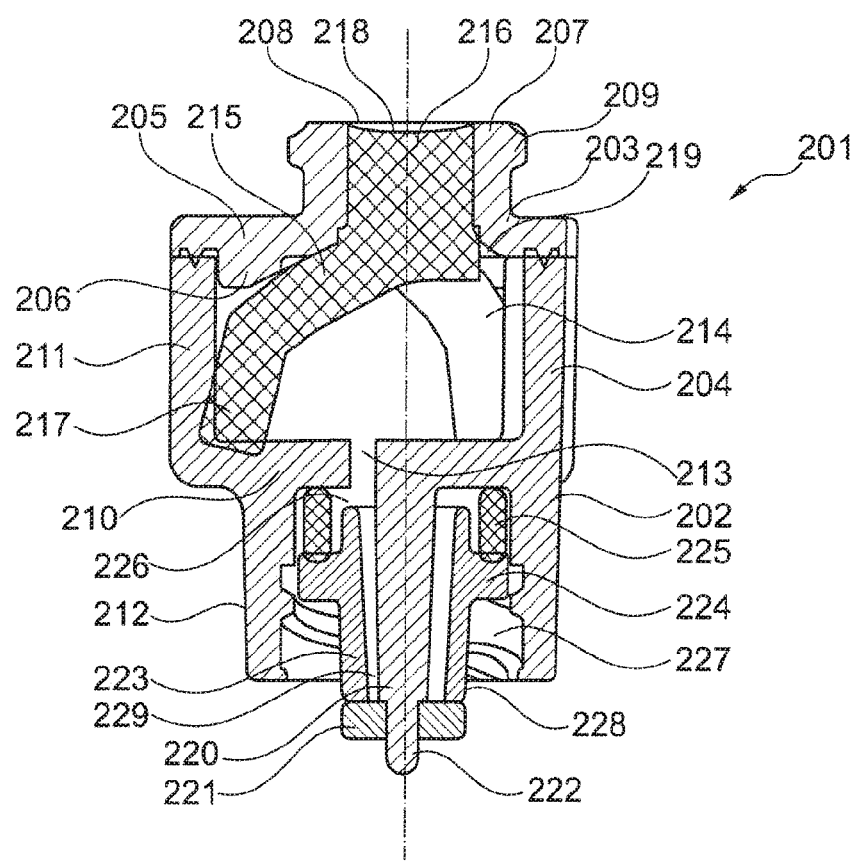
FIG. 9 is a section through another exemplary embodiment of a connecting element according to the invention.

As can be seen in FIG. 9, the two housing parts 203, 204 are connected to one another in the region of the surrounding wall 211 and the floor 205, preferably welded, for instance.

The housing forms a first receiving space 214 in the region of the connection of the two housing parts 203, 204, wherein the receiving space 214 is formed by a surrounding wall 211, a floor 205 of the first housing part, and a floor 210 of the second housing part.

The connector element 207 is provided toward the top on the floor 205 of the first housing part 203.

Figures 10, 11:
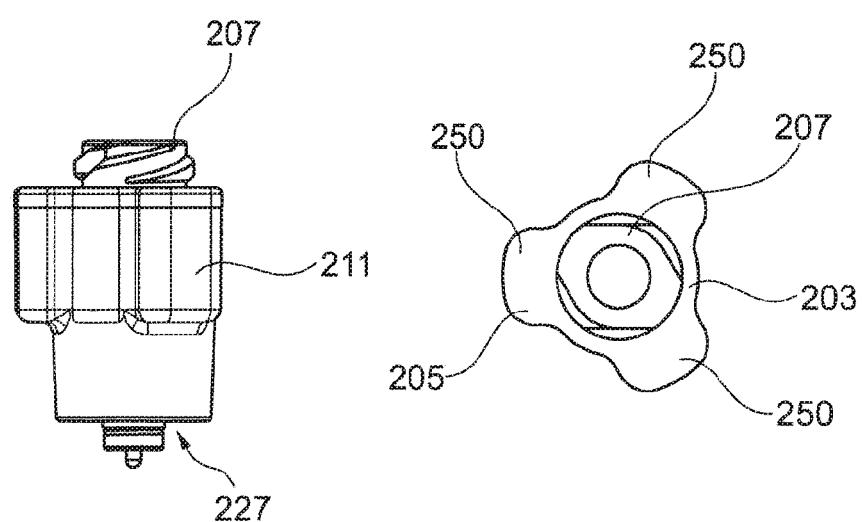
FIG. 10 is a side view of a connecting element from FIG. 9.
FIG. 11 is a view from above of the connecting element from FIG. 9 or 10.
Figure 12:
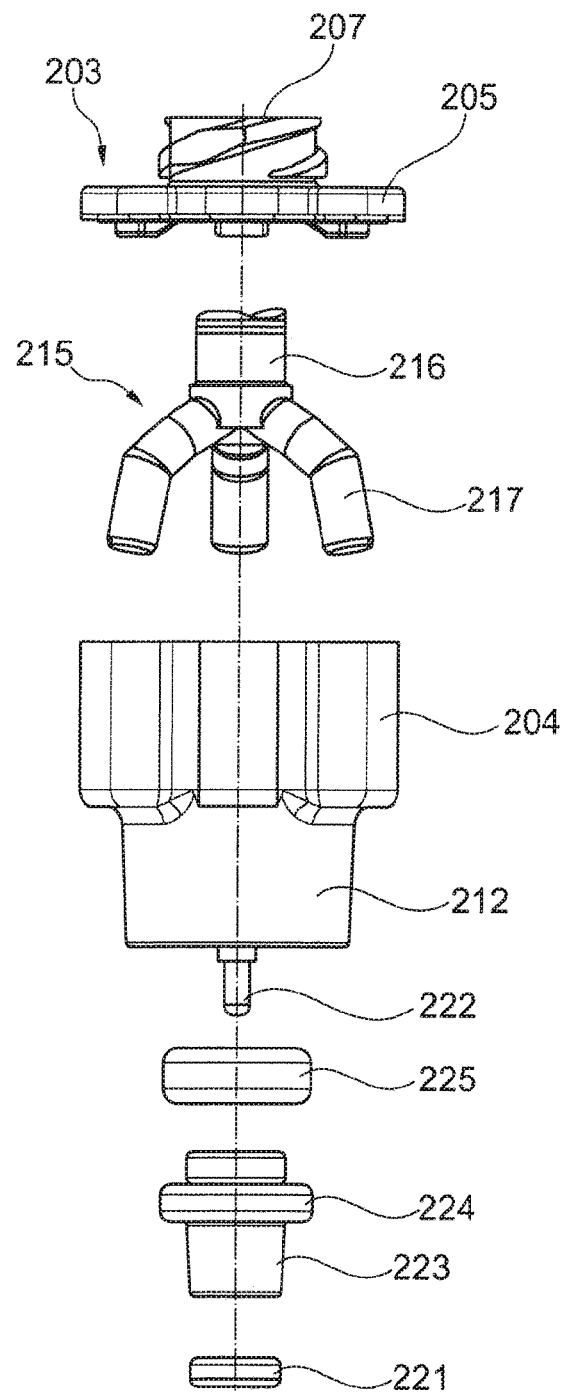
FIG. 12 is an exploded view of the connecting element from FIG. 9.

The valve element 215 is arranged in the receiving space 214 and has a cylindrical region 216 or else a cylindrical body 216, from which resilient arms 217 project downward. In this design, the cylindrical region 216 advantageously is implemented as a single piece with the resilient arms 217, and the resilient arms 217 project radially outward at an angle to the vertical and downward from the cylindrical region 216. The elastic spring element is explained in detail in FIGS. 21 to 24. The resilient arms 217 in the exemplary embodiment from FIGS. 9 to 11 are angled or have bends. When three resilient arms 217 are present, the resilient arms 217 form an arrangement approximating an edge arrangement of a tetrahedron.

In the position of the valve element 215 shown in FIG. 9, a fluid connection between the connector element 207 and the receiving space 214 is closed and sealed. If an element is inserted into the connector element 207 from above, then the cylindrical region 216 of the valve element 215 is loaded downward or compressed, and pushed downward so that the resilient arms 217 bear against the floor of the receiving space 214 and are elastically deformed. This will continue to take place until a fluid connection is present between the channel 218 and a curvature 219 in the region of the connector element. Then a fluid connection can take place between the element to be connected and the receiving space 214. Instead of the curvature, grooves or channels can also be provided in the wall of the connector element that permit a fluid connection starting from a certain, predefinable position of the valve element.

When the element to be connected is removed from the connector element 207 again, then the elastic, deformable valve element 215 relaxes again, and the cylindrical region 216 is pushed upward again so that the connector element 207 is sealed once again.

Provided in the bottom region of the connecting element 201, radially inside the cylindrical wall region 212, is a pin 220 that bears a thickened element 221 at its end, into which a peg 222 of the pin 220 preferably is inserted or preferably is made as a single piece with the pin 220. The element 221 preferably is attached by means of heat staking of the peg.

The pin 220 preferably can be formed as a single piece with a web that separates the openings 213.

A sleeve-like element 223 that transitions into a flange 224 is provided as the valve element, wherein the sleeve-like element 223 is made in the approximate shape of a hollow cylinder and its axial bottom edge region braces against a shoulder of the element 221. Located between the flange 224 and the floor 210 of the housing part is a force accumulator 225, preferably in the form of an annular, elastic element such as an O-ring, in order to effect a loading of the sleeve-like element 223 against the element 221. As a result, a seal is achieved between the receiving space 226 and the connector element 227, which is formed by the sleeve-like element 223 with the floor 224 and the circumferential wall 212.

When an element to be connected having a circumferential collar is inserted into the region 227 from below, the sleeve-like element 223 with the flange 224 is pushed axially upward, in opposition to the force of the force accumulator 225, and the shoulder 228 of the sleeve-like element 223 lifts away from a shoulder of the element 221 and permits a fluid connection to be made from the element to be connected, through the channel 229 in the sleeve-like element 223, to the receiving space 226. Since a fluid connection exists between the receiving space 226 and the receiving space 214 due to the openings 213, a fluid connection can be produced between two elements to be connected that are attached to the connector elements 207 and 227.

Preferably the elastic elements 215 and 225 are made of an elastomeric material, and the housing elements 203, 204 as well as the sleeve-like element 223 and the element 221 are made of a non-elastomeric material that tends to be dimensionally stable, such as a thermoplastic. The element 215 and the element 225 preferably can be made of liquid silicone rubber (LSR) or high temperature vulcanized silicone rubber (HTV) or room temperature vulcanized silicone rubber (RTV), and the housing parts, sleeve, and terminating element 221 can be made of acrylonitrile butadiene styrene (ABS), polycarbonate (PC), polypropylene (PP), or polyethylene (PE), or the like.

FIG. 10 shows a view of the connecting element 201, while FIG. 11 shows that the receiving space 214 with the cover 205 is designed to be round in cross-section with outwardly projecting pockets 250. This means that the cross-section in the region of the pockets has a larger diameter, and is reduced in diameter between the pockets. This has the result of a smaller volume in the receiving space 214.

Figure 13:
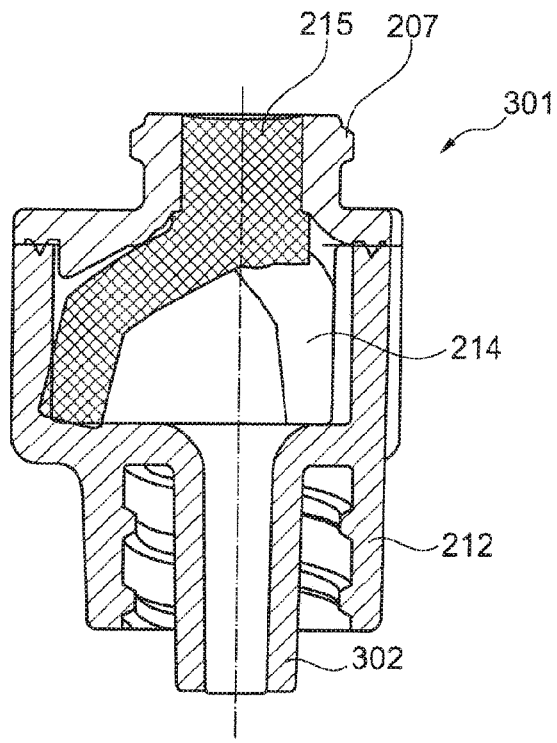
FIG. 13 is a section through another exemplary embodiment of a connecting element according to the invention.
Figure 14:
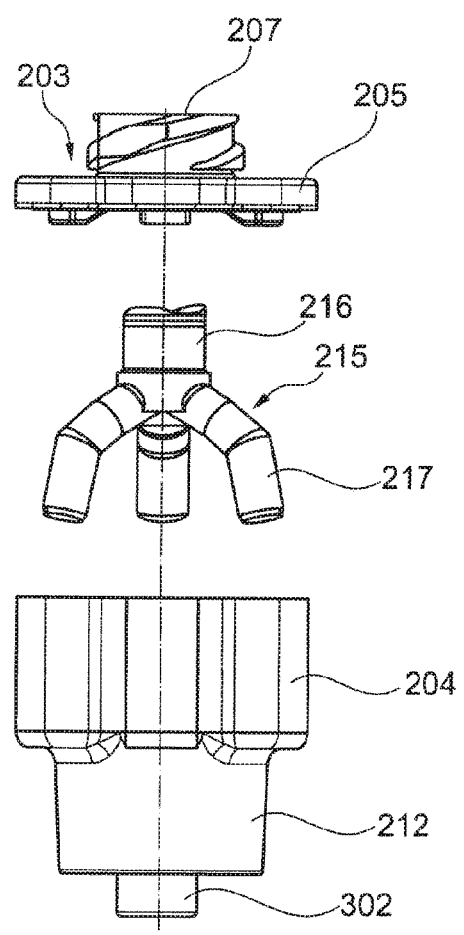
FIG. 14 is an exploded view of the connecting element from FIG. 13.

FIGS. 13 and 14 show another exemplary embodiment of a connecting element 301 according to the invention, in cross-section or in an exploded view, respectively.

It is evident that the connecting element 301 differs from the connecting element 201 in that the sealing unit with pin 220, sleeve 223, and resilient ring 225 is not provided, but instead only a tubular fitting 302.

The remaining identical components have already been described under FIGS. 6 through 11, so the reader is referred to said description.

Figure 15:
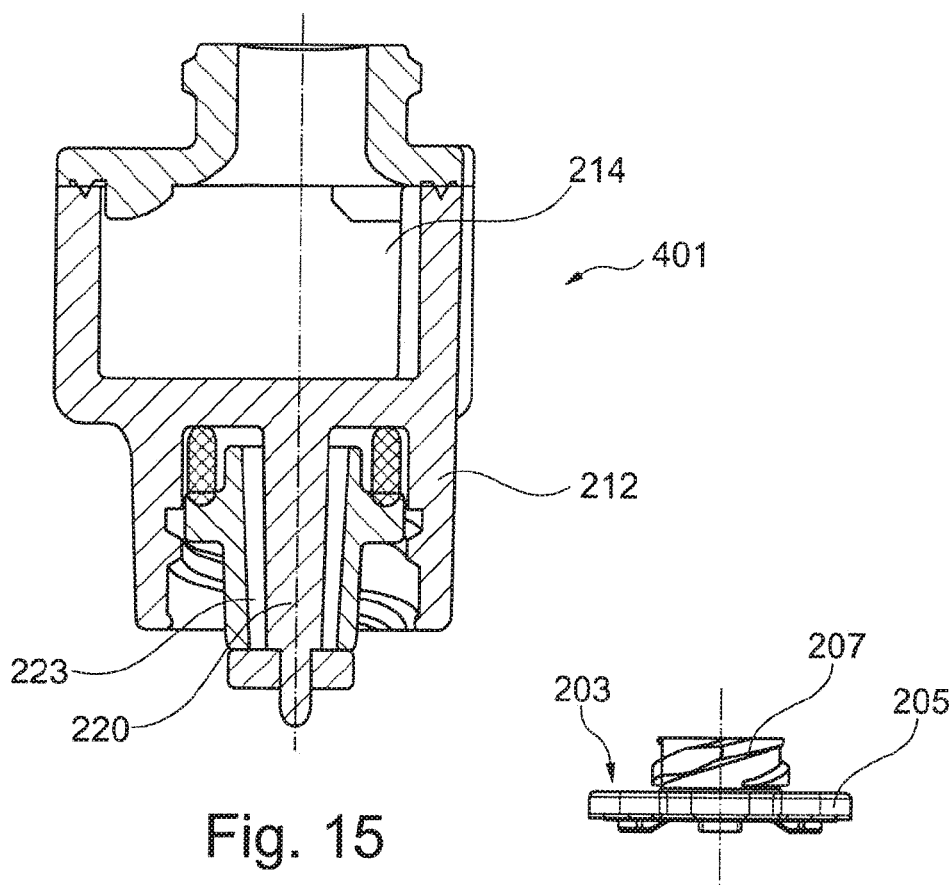
FIG. 15 is a section through another exemplary embodiment of a connecting element according to the invention.
Figure 16:
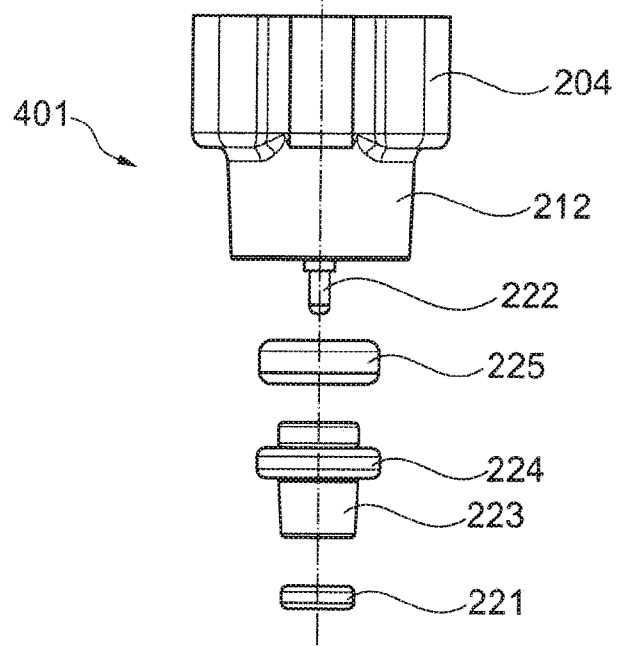
FIG. 16 is an exploded view of the connecting element from FIG. 15.

FIGS. 15 and 16 show another exemplary embodiment of a connecting element 401 according to the invention, in cross-section or in an exploded view, respectively.

It is evident that the connecting element 401 differs from the connecting element 201 in that the sealing unit with the spring element 215 is not provided.

The remaining identical components have already been described under FIGS. 6 through 11, so the reader is referred to said description.

Figure 17:
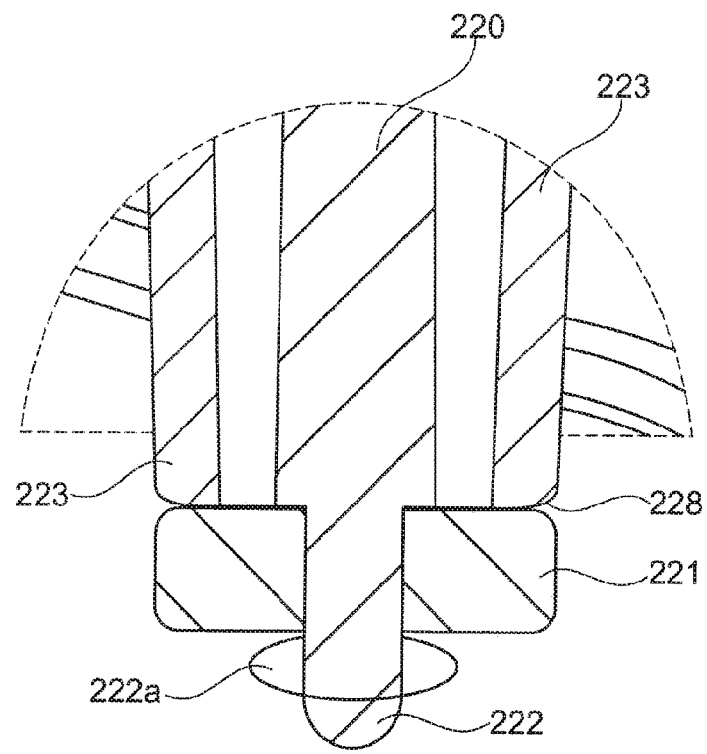
FIG. 17 is a representation of a detail of the connecting element from FIG. 9 in the closed state.
Figure 18:
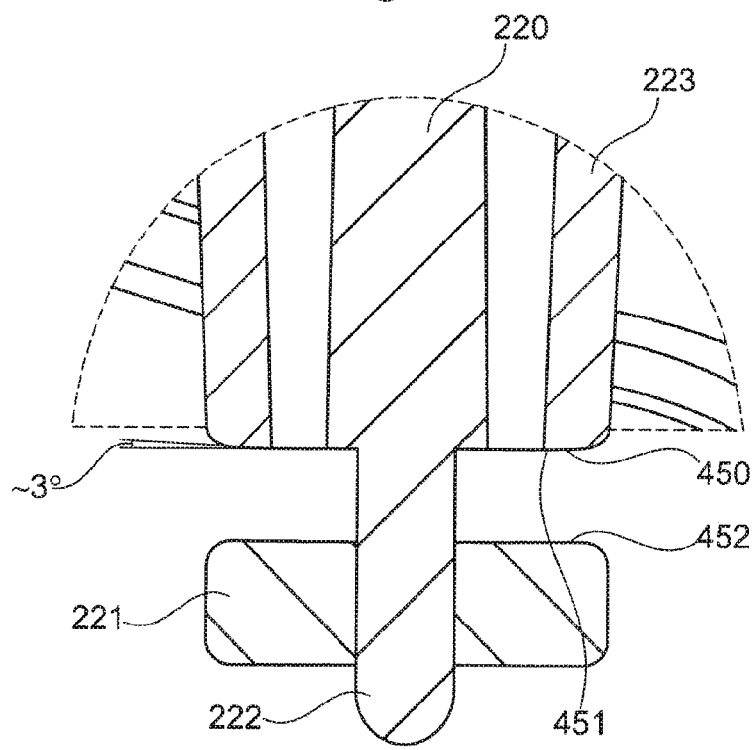
FIG. 18 is a representation of a detail of the connecting element from FIG. 9 in the open state.

FIGS. 17 and 18 show the sealing of the elements 123 and 121 or 223 and 221 against one another. Here, the element 221 is connected to the pin 220, for example by heat staking. To this end, the projecting part of the finger 222 is heat staked so that it forms a sort of lentil shape 222a.

The bottom edge 450 of the element 223 has an angle of approximately 2° to 4°, preferably 3°, to the horizontal so that the inner edge 451 of the element 223 contacts the surface 452 of the element 221 first.

In FIG. 17 the fluid connection is closed or interrupted, and in FIG. 18 the fluid connection is enabled because the element 223 is lifted away from the element 221.

Figure 19:
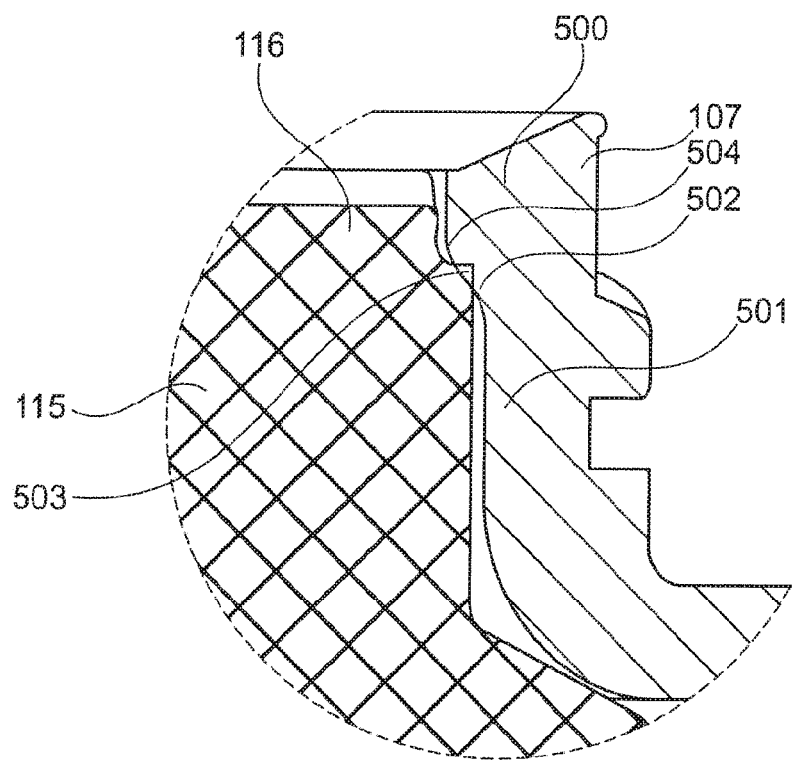
FIG. 19 is a representation of a detail of the connecting element from FIG. 6.
Figure 20:
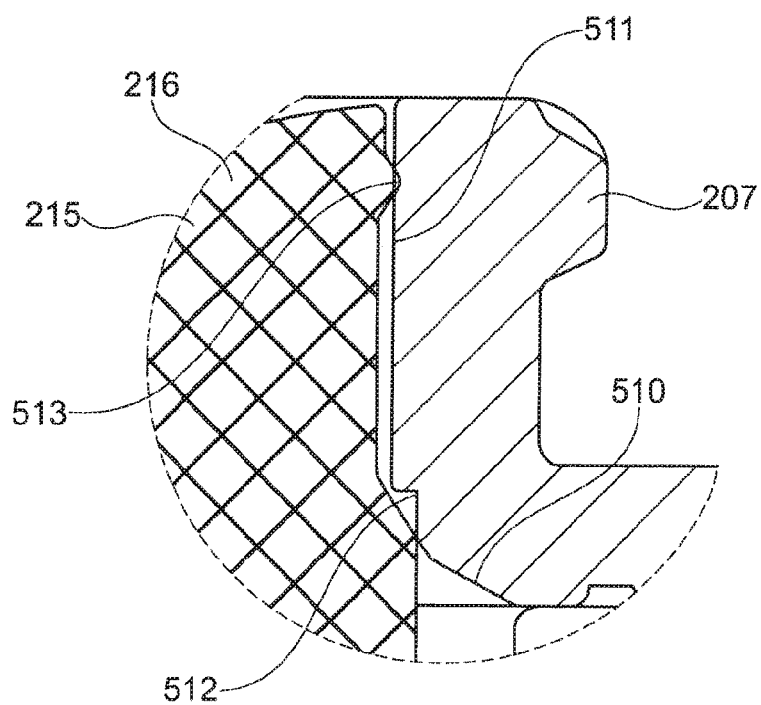
FIG. 20 is a representation of a detail of the connecting element from FIG. 9.

FIGS. 19 and 20 show two embodiments of the seal between the connector element 107 or 207 and the cylindrical region 116 or 216 of the spring element 115 or 215.

FIG. 19 shows the cylindrical region 116 of the elastic spring element 115 in the connector element 107 in cutaway view. At its top end region 500, the connector element 107 has a reduction in diameter, so the diameter in the top end region 500 is smaller than in the region 501 below it. The transition 504 takes place with a designated radius at 502. The elastic element 115 likewise has a radius change at its cylindrical region 116, with the radius in the top region being smaller than the radius in the bottom region. Here, the radius difference is formed by a shoulder, which can essentially be viewed as a right-angled step 503.

If the cylindrical region 116 of the elastic element 115 is in its top position, then the step 503 abuts the transition 504 and makes sealing contact with the transition 504.

FIG. 20 shows a connector element 207 that is essentially tubular inside, with an essentially straight, tubular region 511 that transitions into a widened region 510 in the bottom region.

In the upper region of its cylindrical region 216, the elastic spring element 215 has a sealing lip 513 that projects in the radial direction, and in the bottom region the spring element has a step 512 for enlarging the diameter.

When the cylindrical region 216 is in its upper position, the sealing lip 513 makes sealing contact with the tubular connector element 207, and the step 512 makes sealing contact with the widened region 510 of the connector element 207.

Figure 21:
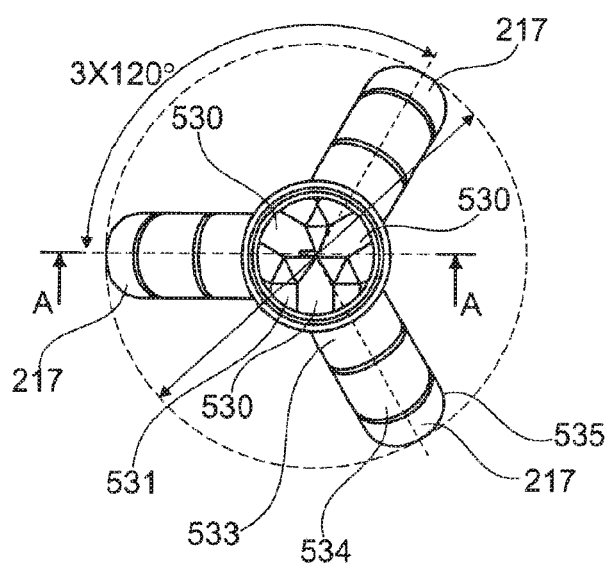
FIG. 21 is a view from above of the elastic spring element.

FIGS. 21 to 24 show different views of the elastic spring element. Visible in the top view shown in FIG. 21 is the cylindrical region 216, which has a structure on its top that shows a three-way passage or a passage with three recesses 530 that converge in a shape somewhat like a star. Each of the recesses 530 are separated from one another by raised areas 531.

Three resilient arms 217 project from the cylindrical region 216, wherein the resilient arms 217 enclose an angle of 120° with one another. They preferably lie in a plane perpendicular to the longitudinal axis of the cylindrical region 216.

The projecting resilient arms 217 advantageously are implemented as straight resilient arms or as resilient arms 217 with one or multiple bends or curves. In the exemplary embodiment from FIGS. 21 to 24, the resilient arms 217 are implemented with bends.

To this end, the resilient arms 217 have a first region 533 that is arranged at an angle α1 of approximately 25° to 30°, preferably 27°, to the plane perpendicular to the longitudinal axis of the cylindrical region 216.

In addition, the resilient arms 217 have a second region 534 that is arranged at an angle α2 of approximately 35° to 40°, preferably 37°, to the plane perpendicular to the longitudinal axis of the cylindrical region 216.

Also, the resilient arms have a third region that is arranged at an angle α3 of approximately 75° to 80°, preferably 77°, to the plane perpendicular to the longitudinal axis of the cylindrical region 216.

The first region 533 adjoins the cylindrical region. This region is adjoined by the region 534, which is adjoined by the region 535.

Figure 23:
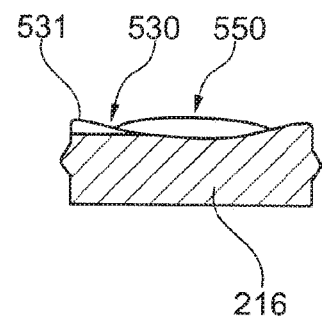
FIG. 23 is a section through the elastic spring element along line B-B from FIG. 22.
Figure 22:
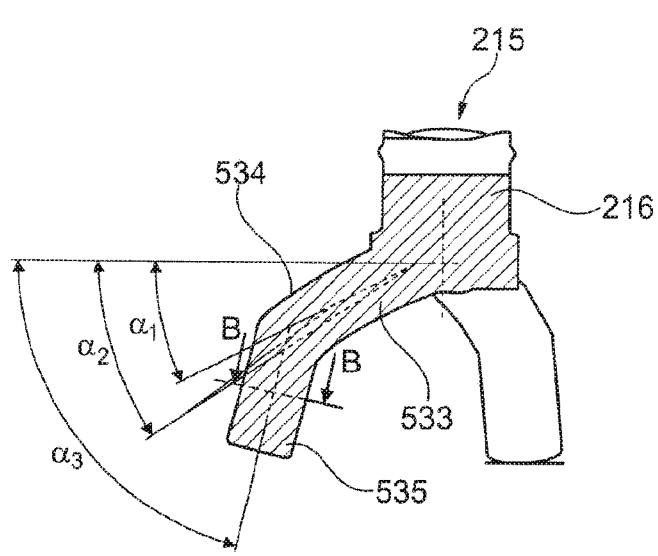
FIG. 22 is a section through the elastic spring element along line A-A from FIG. 21.

FIG. 23 shows the surface 550 of the cylindrical region 216 in a side view. The structure of the surface 550 with the recesses 530 and the raised areas 531 can be seen.

Figure 24:
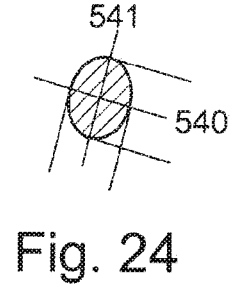
FIG. 24 is an enlarged detail view of the top region of the elastic spring element from FIG. 22.

The cross-section of the resilient arms is oval as shown in FIG. 24. Here, the axis 540 in the short direction points toward the cylindrical region 216, and the axis 541 in the long direction is perpendicular thereto. This achieves the result that the resilient arms 217 are easier to deform in the direction of motion of the resilient arms 217 than in the direction perpendicular thereto, which increases lateral stability against twisting. Alternatively, the cross-section can also have a round or other shape.

With regard to the cross-sections of the resilient arms, the arms can all be identical in design. One of the resilient arms can also be designed differently from the other resilient arms, in particular with a larger cross-section or with a smaller cross-section, for instance. Alternatively, the resilient arms can also all be designed differently from one another, for example with a larger or smaller cross-section.

This has the effect that, when the cylindrical region is loaded from above by the connector element from the direction of the inlet opening, the cylindrical region can tilt at least slightly in its final position. This has the advantage that the face of the cylindrical element permits good flow through the connecting element, even when it is smooth in design without channels.

The invention also includes an exemplary embodiment that is mirror-imaged at the floor 10, unlike the exemplary embodiment from FIGS. 1 and 2, and has the top part of the device or the bottom part of the device in duplicate.

The same applies to an exemplary embodiment that corresponds essentially to the embodiments from FIG. 6, but with mirror-imaging with regard to the floor 110 so that the top part or the bottom part is duplicated.

The same applies to an exemplary embodiment that corresponds essentially to the embodiments from FIG. 9, but with mirror-imaging with regard to the floor 210 so that the top part or the bottom part is duplicated.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An elastic spring element with a cylindrical body and resilient arms projecting therefrom, the spring element being made of an elastic material, wherein the cylindrical body has a first end and a second end, the resilient arms projecting from the second end of the cylindrical body, wherein the cylindrical body includes a first circumferential sealing lip adjacent to the resilient arms, such that the first circumferential sealing lip is positioned between the first end and a transition of the cylindrical body to the resilient arms at the second end, wherein the first circumferential sealing lip is a circumferential shoulder that protrudes from an exterior surface of the cylindrical outer wall of the cylindrical body in a radial direction, wherein the cylindrical body has a second circumferential sealing lip adjacent to the first end, such that the first circumferential sealing lip is positioned between the second circumferential sealing lip and the resilient arms, wherein the second circumferential sealing lip is a circumferential rib that protrudes from the exterior surface of the cylindrical outer wall of the cylindrical body in the radial direction, wherein the first circumferential sealing lip and the second circumferential sealing lip are spaced apart from each other on the exterior surface of the cylindrical outer wall in an axial direction of the cylindrical body, wherein the cylindrical outer wall of the cylindrical body, extending from the first circumferential sealing lip to the second circumferential sealing lip, has a constant diameter, and wherein, in a tension-free state of the elastic spring element, a distal end face of the first end of the cylindrical body has recesses and raised areas, wherein adjacent recesses are separated by a respective one of the raised areas, and the raised areas extending from the distal end face in the axial direction of the cylindrical body.

2. The elastic spring element according to claim 1, wherein the resilient arms are straight resilient arms or resilient arms with one or multiple bends or curves.

3. The elastic spring element according to claim 1, wherein the resilient arms are arranged at an angle of 120° with respect to one another in a plane perpendicular to a longitudinal axis of the cylindrical body.

4. The elastic spring element according to claim 1, wherein the resilient arms have a first region that is arranged at an angle of approximately 25° to 30° or at 27° to a plane perpendicular to a longitudinal axis of the cylindrical body.

5. The elastic spring element according to claim 4, wherein the resilient arms have a second region that is arranged at an angle of approximately 35° to 40° or at 37° to a plane perpendicular to a longitudinal axis of the cylindrical body.

6. The elastic spring element according to claim 5, wherein the resilient arms have a third region that is arranged at an angle of approximately 75° to 80° or at 77° to a plane perpendicular to a longitudinal axis of the cylindrical body.

7. The elastic spring element according to claim 1, wherein a cross-section of each of the resilient arms is round or oval or polygonal.

8. The elastic spring element according to claim 1, wherein a cross-section of each of the resilient arms is oval, such that the cross-section has two different diameters.

9. The elastic spring element according to claim 1, wherein the resilient arms have multiple bends.

10. The elastic spring element according to claim 1, wherein the cylindrical body, the first circumferential sealing lip and the second circumferential sealing lip are made of a same material.

11. The elastic spring element according to claim 1, wherein the distal end face, having the recesses and raised areas, is spaced apart from the second circumferential sealing lip in the axial direction of the cylindrical body.

* * * * *